United States Patent [19]

Schnall

[11] Patent Number: 5,720,709

[45] Date of Patent: Feb. 24, 1998

[54] APPARATUS AND METHOD FOR MEASURING RESPIRATORY AIRWAY RESISTANCE AND AIRWAY COLLAPSIBILITY IN PATIENTS

[75] Inventor: Robert Schnall, Kiryat-Bialik, Israel

[73] Assignee: S.M.C. Sleep Medicine Center, Haifa, Israel

[21] Appl. No.: 691,182

[22] Filed: Aug. 1, 1996

[30] Foreign Application Priority Data

Oct. 25, 1995 [IL] Israel ......................................... 115.760

[51] Int. Cl.$^6$ ................................................. A61M 16/00
[52] U.S. Cl. .................... 600/538; 600/529; 128/204.24; 128/204.23
[58] Field of Search ..................... 128/716, 718, 128/720, 725, 728, 204.21, 204.23

[56] References Cited

U.S. PATENT DOCUMENTS

| | | | |
|---|---|---|---|
| 4,122,839 | 10/1978 | Franetzki et al. | 128/720 |
| 4,220,161 | 9/1980 | Berlin et al. | 128/720 |
| 4,259,967 | 4/1981 | Vooren et al. | 128/720 |
| 5,060,655 | 10/1991 | Rudolph | 128/725 |
| 5,233,998 | 8/1993 | Chowienczyk et al. | |
| 5,456,264 | 10/1995 | Series et al. | 128/725 |
| 5,490,502 | 2/1996 | Rapoport et al. | 128/725 |
| 5,522,397 | 6/1996 | Vermaak | 128/725 |
| 5,535,739 | 7/1996 | Rapoport et al. | 128/725 |
| 5,582,182 | 12/1996 | Hillsman | 128/720 |

FOREIGN PATENT DOCUMENTS

| | | | |
|---|---|---|---|
| 0627196 A1 | 12/1994 | European Pat. Off. | |
| 4034176 | 11/1991 | Germany | 128/720 |

*Primary Examiner*—Jennifer Bahr
*Assistant Examiner*—Stephen Huang
*Attorney, Agent, or Firm*—Frishauf, Holtz, Goodman, Langer & Chick

[57] ABSTRACT

An apparatus for measuring the airways resistance of a person by short-time occlusion of inhalation, includes a face mask having an inlet channel and an outlet channel, the latter provided with an outlet valve, and a narrow passage close to a plenum in front of the face. A pneumotachograph is mounted in the narrow passage and is connected to indicating and recording instrumentation. An elastic balloon filled with a liquid is positioned in the inlet channel and is configured to be fully inflated until total occlosure of the inlet channel and to be completely deflated to allow free air passage therethrough. Inflation and deflation of the balloon is manually performed by means of a syringe which is connected to the balloon by flexible tubing, with both syringe and tubing filled with liquid.

11 Claims, 6 Drawing Sheets

FIG-5 the airflow resistance and collaps-
APPARATUS AND METHOD FOR MEASURING RESPIRATORY AIRWAY RESISTANCE AND AIRWAY COLLAPSIBILITY IN PATIENTS The invention relates to an apparatus and method for measuring and recording the airflow resistance and collapsibility of the respiratory airways in humans for medical, diagnostic, clinical, physiological or other testing and evaluation purposes. It relates particularly to apparatus suitable for non-invasive and ready application to a person, whether awake or asleep.

BACKGROUND OF THE INVENTION

Apparatus for measuring airways resistance in human subjects are known in medicine and science, but to our knowledge none of these apparatus is adapted for non-invasively and simultaneously measuring of both airways resistance and airways collapsibility.

Non-invasive apparatus were developed to avoid using the unpleasant and non-physiological, direct methods of measuring flow resistance which require the placement of presssure measuring tubes in the upper airway or of lowering a balloon into the esophagus, and there exist a relatively large number of apparatus for this purpose. Some of these employ the principle of completely occluding inhalation or exhalation during a small time interval and measuring air flow and pressure both during and immediately after occlusion. Other apparatus are built on the principle of periodically increasing the flow resistance to and from the person's airways opening to the atmosphere and calculating the airways resistance from the resulting measurements of pressure and airflow through the apparatus. The airway resistance while using the method of complete occlusion during a small time interval can be calculated by the equation:

$$R=(P_o-P_u)/F_u,$$

wherein

R=Airway resistance, $P_o$=pressure during occlusion, $P_u$=pressure while unoccluded, and just before the occlusion, $F_u$=Flow unoccluded.

An apparatus for this kind of measurement is disclosed in U.S. Pat. No. 5,233,998 (CHOWIENCZYK): The apparatus includes a housing, a cylindrical bore extending through the housing and a devices for measuring the flow through the bore caused by a person inhaling or exhaling through the bore. An elliptically shaped plate-valve is configured to open the passage through the bore and to obstruct it completely during short time intervals. A pressure gauge measures and records the pressure variations in relation to the airflow through the bore permitting the calculation of the resistance of the person's airways.

The main drawbacks of this embodiment are the impossibility to apply the apparatus to a sleeping subject, and that there is no way to define the collapsibility of the airways.

The airways resistance while using the method of added flow resistance is calculated by the following equation:

$$R=R_a\times(F_u-F_o)/F_o,$$

wherein

R=Airway resistance, $R_a$=Added resistance, $F_u$=flow with ambient resistance, $F_o$=Flow with added resistance.

A typical apparatus for measuring a person's airways resistance by this second method is disclosed in European Patent Application No. 94301706.1 (VERMAAK). The apparatus includes a pneumotach connected in series with the person's airway with pressure measuring means, positioned upstream and downstream of a fixed resistance element. It further includes a removable second resistance element in series with the first element. By measuring the pressure upstream and downstream of the fixed resistance element by pressure sensors, while the second resistor is alternately in place or removed and recording the respective pressure differential curves, it becomes possible to calculate the airway resistance.

The drawback of this apparatus is—again—the impossibility to use the apparatus with sleeping persons and that it can be applied to expiration only.

Still another device for the measurement of airways resistance is disclosed in U.S. Pat. No. 4,220,161 (BERLIN). It includes cyclic perturber means affixed to an expiration passage in the form of a sectored member traversing the passage and means for measuring the disparities caused by the changing resistance.

Again, as in the former case, the device is not suitable for use with sleeping persons. Furthermore, the magnitude of the disparities caused by the changing resistances is proportional to the differences of the resistances and thus, likewise, is the accuracy of the measurements. Additionally, a finite period of time is required for the transition between the two resistance levels. During this time it is highly probable that the driving force of the respiratory pump will have changed, which may invalidate the measurement since it will be impossible to accurately know to what extent the altered respiratory drive or the changed applied resistance caused the change in flow rate or mouth pressure.

It is, therefore, a main object of the invention to provide apparatus configured to both measure the airway's resistance in a person by sudden occlusion and thus to permit definition of the collapsibility of the airways by gradually increasing the flow resistance in the apparatus, while intermittently measuring the airways resistance.

It is another object of the invention to provide apparatus to be operated silently, permitting its use with a person during sleep.

It is another aim to provide apparatus that is readily fastened to the face of a person while he or she is asleep.

Still another object is to provide means for sudden total occlusion and for automatic return to a predetermined flow resistance.

It is a further object to provide apparatus linked to computer means for the sake of obtaining highly accurate results. Also to be used in conjunction with continuous positive airway pressure ventilators, in order to provide feedback to optimize the pressure generated by these devices.

And it is a final object to provide an apparatus which is readily operated without danger to the patient and which lends itself to ready cleaning and sterilizing.

SUMMARY OF THE INVENTION

The apparatus for measuring the airways resistance of a person as well as the collapsibility of his airways upon application of gradually increased flow resistance of the apparatus includes the following items:—a face mask for covering either the nose, or both the mouth and nose at the same time, the mask having a plenum close to the face communicating with the atmosphere by means of an inlet channel and an outlet channel with the latter containing an outlet valve. A pneumotachograph of known design is mounted in the plenum configured to measure and record the air flow through the apparatus during each inhaling and exhaling cycle as well as the pressure during and immediately after total occlusion. Part or total occlusion of the cylindrical inlet channel or outlet channel is effected by an elastic balloon completely filled with a liquid and coaxially mounted in the channel. The balloon is connected through non-elastic piping to a liquid-filled syringe configured to inflate or deflate the balloon to a predesignated volume and diameter in accordance with markings on the unit. In a preferred embodiment of the invention the balloon is connected in parallel to two syringes permitting total momentary occlusion and return to an exact predetermined flow resistance as will be described further on with reference to the accompanying drawings.

In order to prevent exhaled devitalized air from remaining in the inlet channel and from being re-breathed, it is advantageous to provide an inlet valve downstream of the balloon which will thus reduce the effective dead space, leaving less of the respiratory path filled with exhaled air.

DETAILED DESCRIPTION OF THE DRAWINGS

Figure 1:
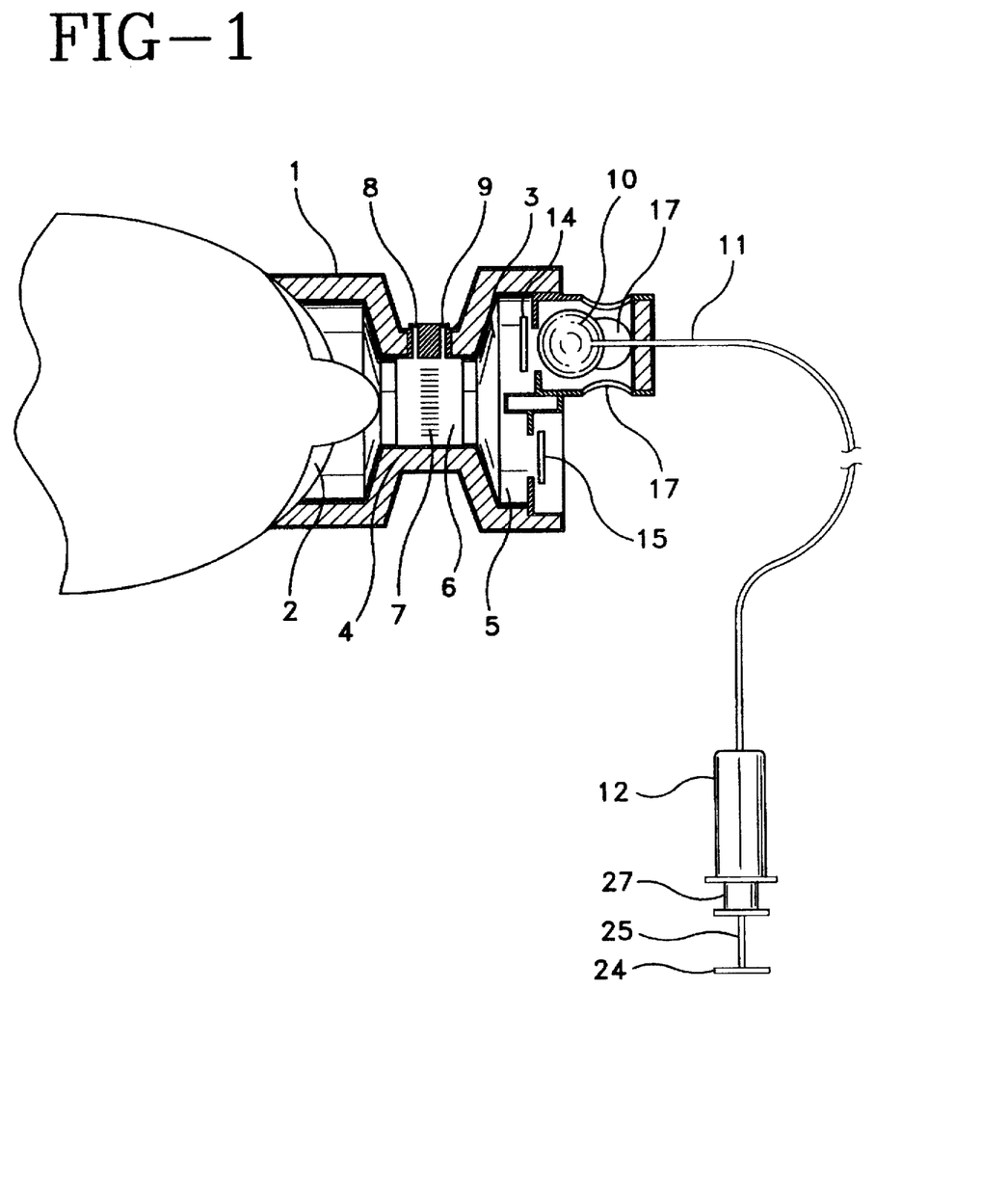
FIG. 1 Illustrates an apparatus for measuring airways resistance connected to a face mask.

The apparatus illustrated in FIG. 1 includes a mask 1 which covers both mouth and nose, but could be adapted for covering the nose only. It is attached to the face by elastic sealing means 2 preventing air from entering the mask except through the inlet channel. The apparatus is enclosed in a solid housing 4 which contains a relatively narrow passage 6 which is continued towards the outside, i.e. the atmosphere, in the form of an inlet channel 3 and an outlet channel 5. Air enters the apparatus by four circular inlet openings 17 perforating the outer end of the inlet channel. A pneumotachograph 7 is mounted in passage 6 and two ports 8 and 9 extending from both sides of the pneumotachograph lead to pressure gauges and means for measuring the air flow rate and pressure differences in a known manner. The data measured are transmitted to computer means configured to display and record the airways resistance of the patient and the collapsibility of his airways by increasing the flow resistance in the inlet channel. Narrowing and total occlusion of the inlet channel is effected by an elastic balloon 10 which is connected by non-elastic tubing 11 to a syringe 12. The entire system is filled with an incompressible liquid configured to keep the balloon inflated to exact predesignated dimensions. In accordance with the degree of inflation the balloon effects obstruction of the inlet channel to the desired flow resistance, or provides free flow by total collapse of the balloon or complete occlusion of the inlet channel by inflation of the balloon until its circumference is pressed onto the channel walls. As can be visualized from the drawing, the apparatus is designed for measuring the airways resistance and collapsibilty during inhalation only, and for this purpose an inlet valve 14 and an outlet valve 15 are mounted across the respective inlet and outlet channels.

Figure 2A:
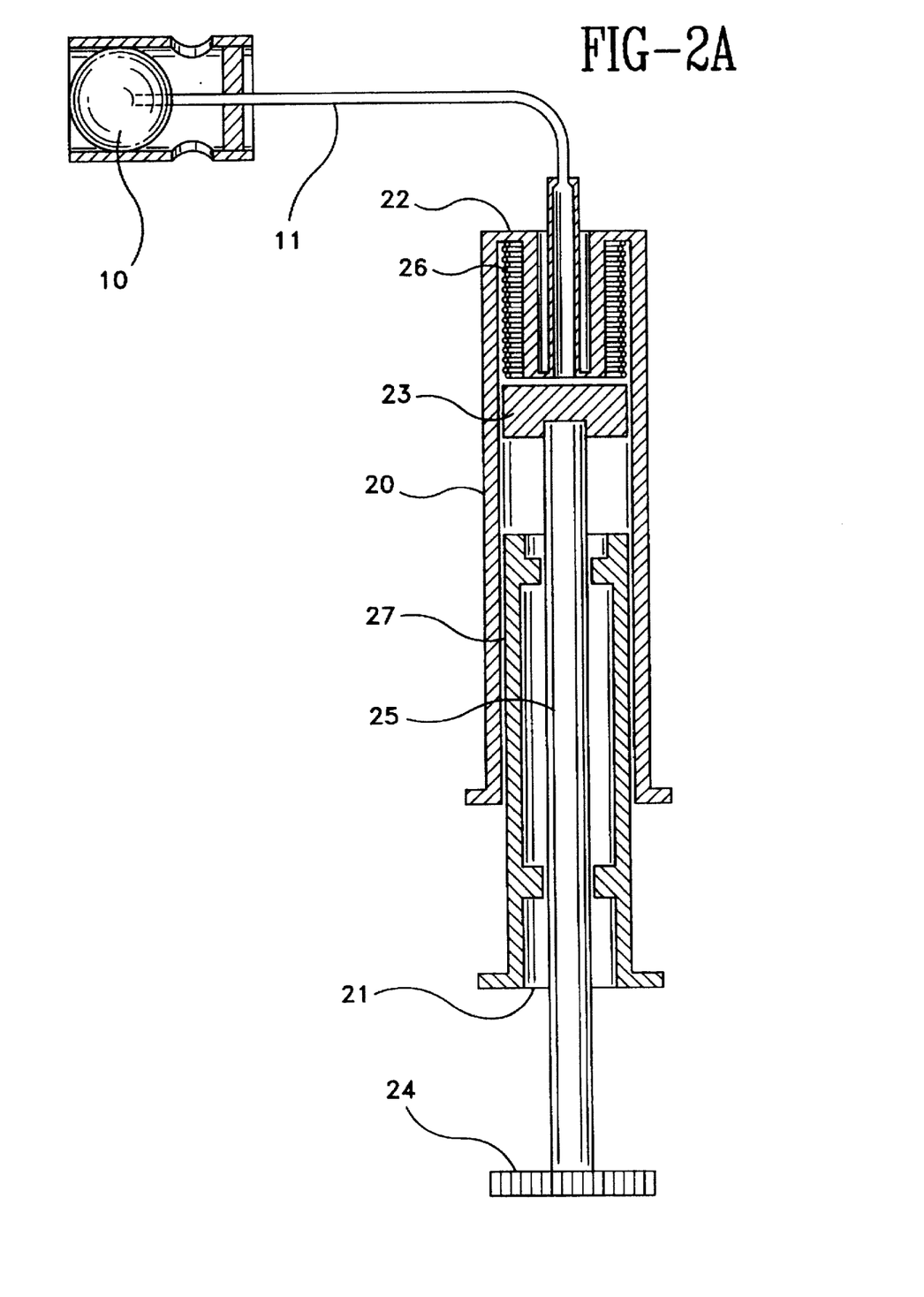
FIGS. 2A and 2B illustrate the syringe configured to control the operation of the apparatus of FIG. 1, in two positions.
Figure 2B:
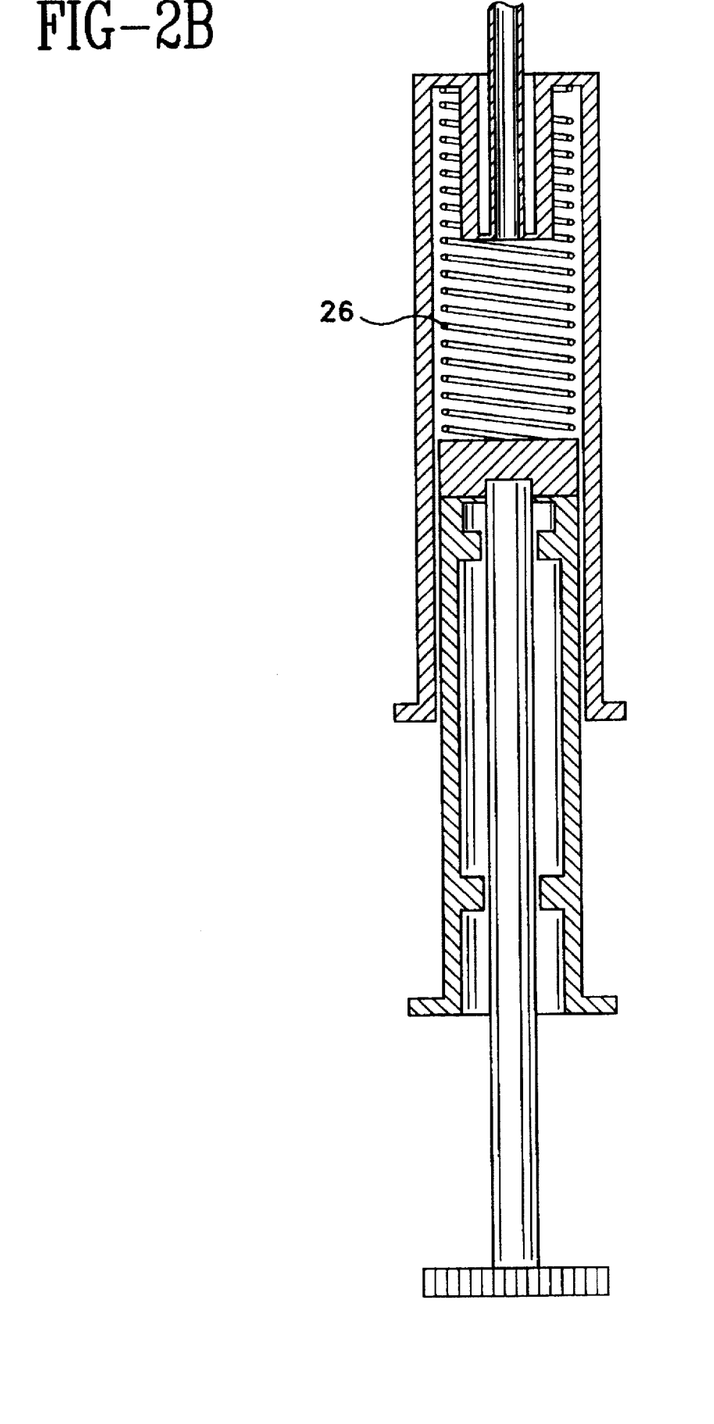

FIGS. 2A and 2B illustrate operation of the balloon by the syringe 12. The unit comprises a cylinder 20 which has an open near end 21 and a closed far end 22 which is connected to the balloon by tubing 11. A piston 23 is longitudinally movable in the cylinder bore and provided with sealing means (not shown) serving to prevent escape of liquid. Manual motion of the piston is by means of a handle 24 and a piston rod 25, and the drawing shows that by pushing the piston towards the far end of the cylinder, the balloon is fully filled with liquid. A helical spring 26 is mounted between the far end 22 and piston 23 urging the piston towards the near end, thereby releasing the liquid out of the balloon. A sleeve 27 is positioned in the cylinder and is adjustable therein by means of screw thread, permitting to change its position at different distances from the far end of the cylinder. For inflating the balloon the piston 23 is pushed into the cylinder by means of the handle (see FIG. 2A), and after release of the handle spring 26 returns the piston 23 until its contact with the far end of sleeve 27 see FIG. 2B), which defines the rate of filling the balloon with liquid and creation of flow resistance in the apparatus.

Figure 3:
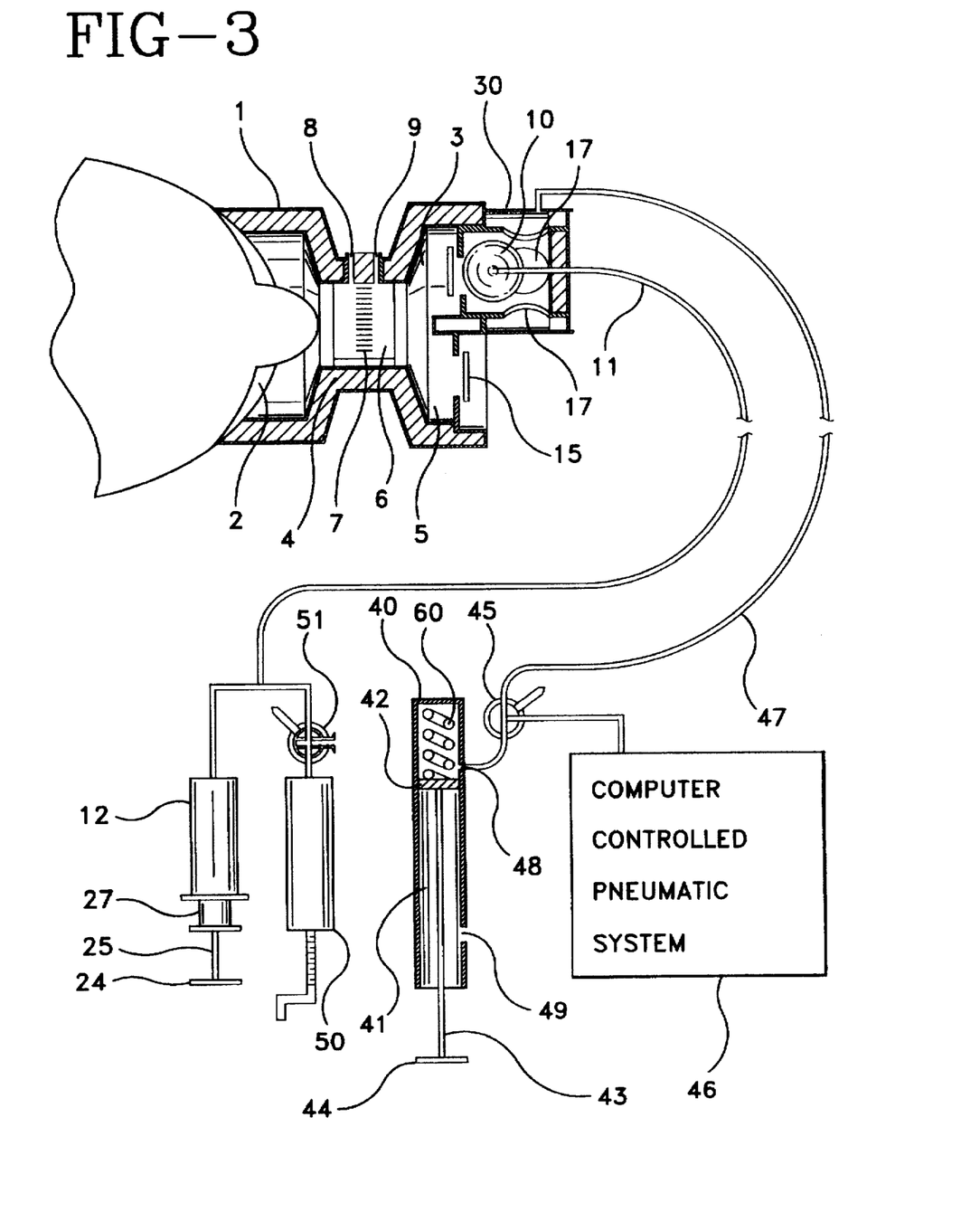
FIG. 3 illustrates an apparatus similar to that shown in FIG. 1, with the addition of a membrane serving to occlude air inlet ports of the apparatus.

The system illustrated in FIG. 3 shows an, additional closing device of the inlet channel in the form of a membrane 30 which can be inflated to close the inlet openings 17, by means of a syringe 40. The system is filled with a gas, preferably air, and the membrane is inflated to close openings 17 of the inlet channel by operation of the syringe. The latter comprises a piston 42 movable in a cylinder 41 by means of a piston rod 43 and a handle 44. By pushing the piston into the cylinder, air is compressed and blocks openings 17, while balloon 10 is being employed for changing the flow resistance inside the apparatus. A change-over valve 45 permits alternative operation of the membrane by a computer-controlled pneumatic system 46.

The pneumatic occlusion system shown in FIG. 3 is designed for effecting very short periods of closure of openings 17 in housing 1 by inflation of membrane 30 by operating the syringe 40. The syringe is connected to the membrane by piping 47 which is connected to an outlet port 48 in cylinder wall 41 which is remote from the distal end. An air inlet opening 49 perforates the cylinder wall close to its proximal end. The operation of closing and opening of membrane 30 is as follows:—piston 42 is pulled back until the piston's distal end is drawn distal to the air inlet opening 49 thus allowing the cylinder to be filled with air. The piston is then pushed inwards thereby inflating the membrane and closing openings 17; as soon as piston 42 has passed outlet opening 48, air is pressed out of the membrane by the latter's elasticity, back into the cylinder and out into the atmosphere through inlet opening 49 as well as through the open cylinder end. A helical spring 60 urges piston 42 back towards its original position and causes a negative pressure to prevail between the membrane 30 and the cylinder wall, thus maintaining the membrane in a collapsed state.

Figure 4:
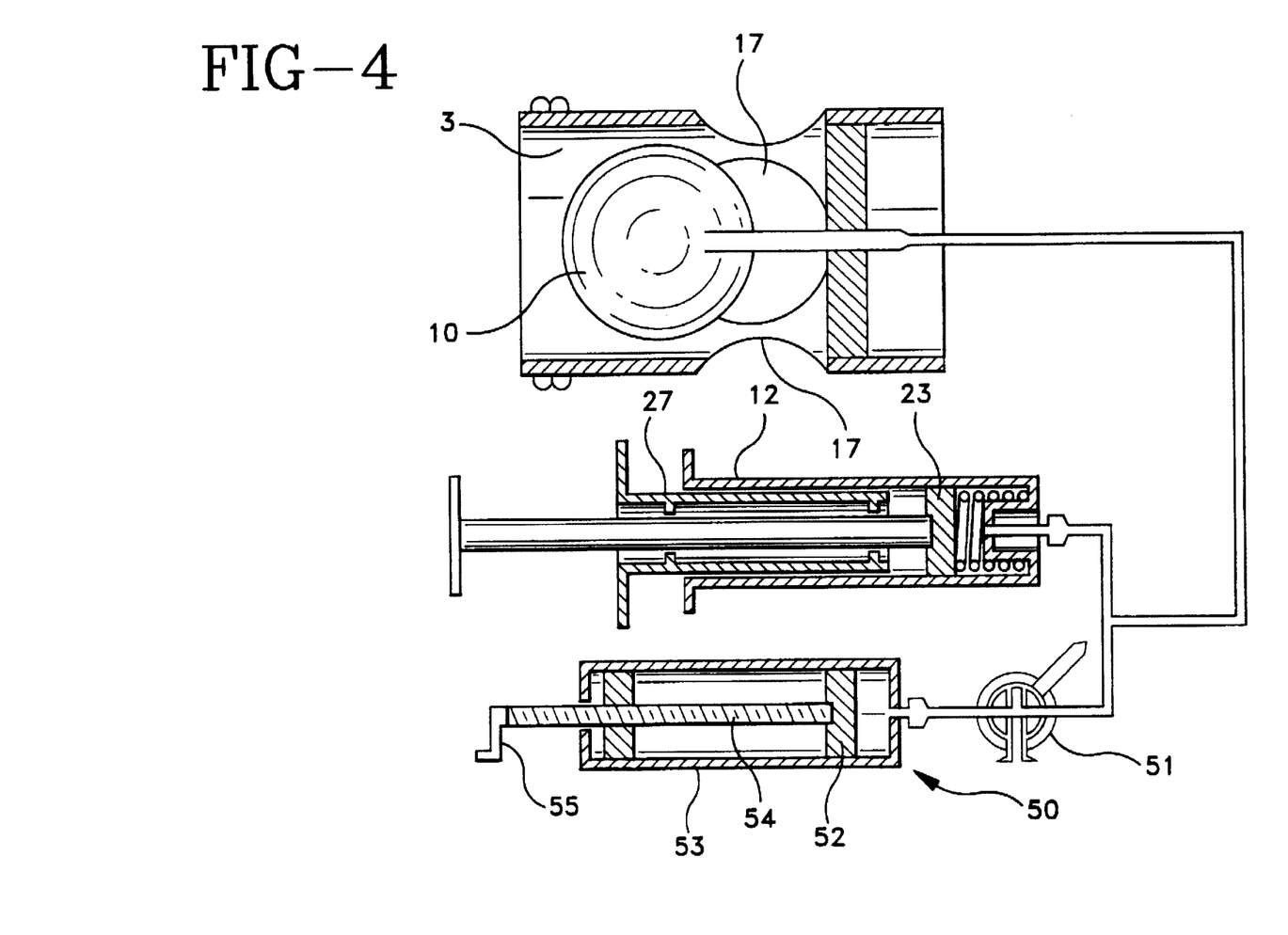
FIG. 4 illustrates an enlarged detail of the control mechanism shown in FIG. 3.

As shown in detail in FIG. 4, the system for filling and emptying of the balloon with liquid comprises the syringe 12 of FIGS. 1 and 2 and an additional syringe 50 communicating with the system via piping 11 with the aid of a two-way valve 51. While syringe 12 is identical with that shown in FIG. 2 and includes a piston and an adjustable sleeve 27, syringe 50 comprises a piston 52 which is lengthwise movable in cylinder 53 by a screw 54 to be rotated by a handle 55. This syringe serves to keep the system filled with water which is liable to evaporate through the wall of the balloon; by opening valve 51 and turning handle 55, water contained in cylinder 50 is pressed into the system for titration, i.e. for adjustment of the balloon volume which should occlude the inlet whenever piston 23 is completely depressed.

Figure 5:
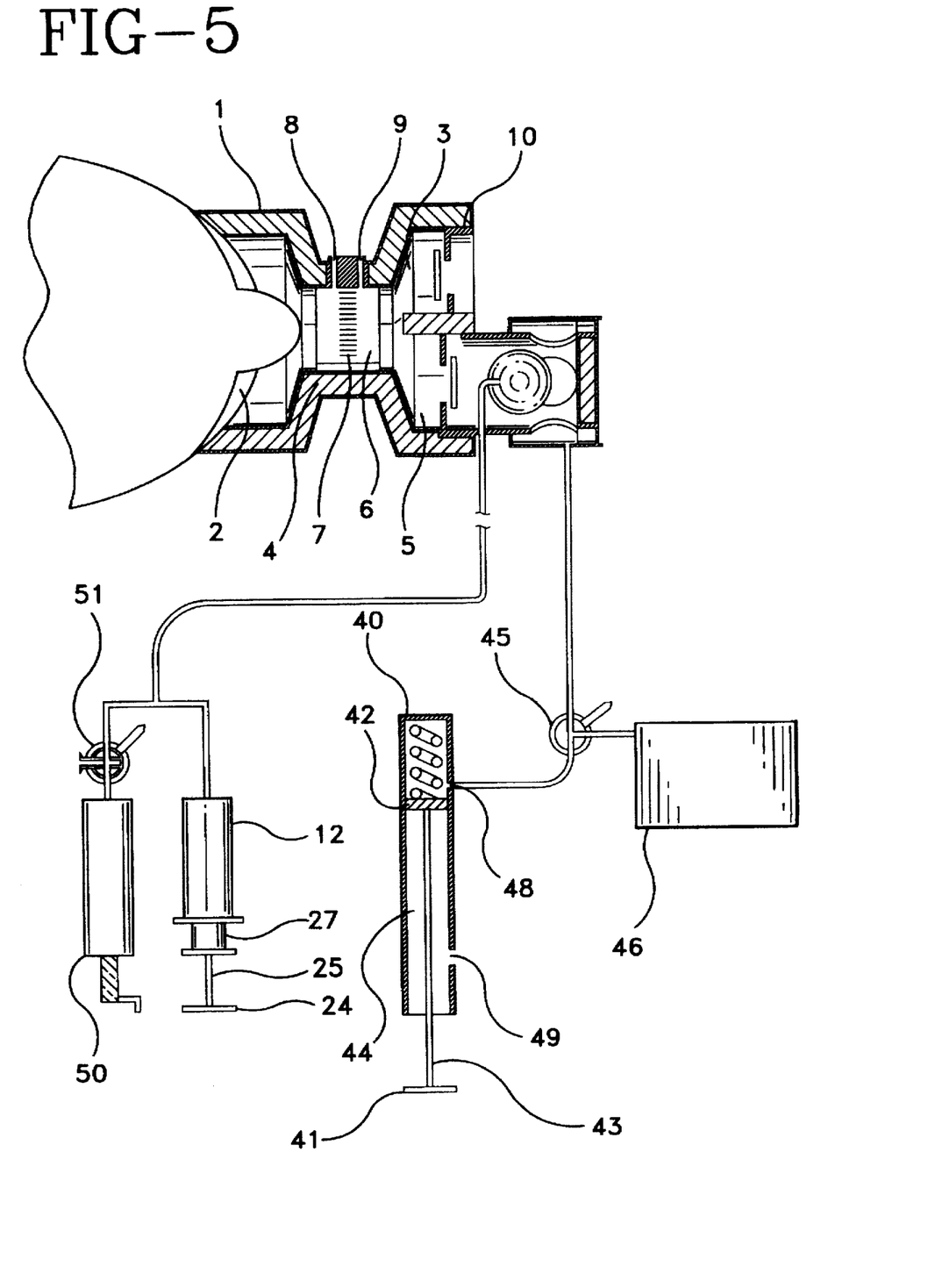
FIG. 5 shows the apparatus having the occlusion device positioned in the outlet channel for measuring airways resistance during exhalation.

FIG. 5 illustrates a face mask provided with closure means in the outlet channel. All components for operation of the apparatus are identical with those shown in connection with the face mask having the closure means mounted in the inlet channel, except for the fact that pipe 11 enters the balloon from the upstream side with the aim to avoiding its deformation by increasing its diameter. Further explanations appear to be superfluous.

The main advantage of the present apparatus is the fact that it retains its level of resistance with changing pressure gradients. Since the balloon is flexible, its diameter perpendicular to the tubular channel decreases with increasing pressure forming an ellipsoid thereby increasing the cross section of the annular orifice formed between balloon and tube. It can be proved that the resistance of the orifice remains substantially identical for different pressure gradients, in contradistinction to fixed non-elastic orifices which behave in a non-linear fashion.

I claim:

1. An apparatus for measuring airways resistance of a person by occluding inhalation of said person during a short interval and for measuring collapsibility of the airways of the person by gradually increasing flow resistance through said apparatus, said apparatus comprising:
   - a face mask of a solid material adapted to be tightly attached to face portions of the person and surrounding at least a nose of the person, said mask having a plenum close to the face portions, continued by a passage of smaller dimensions and an inlet channel and an outlet channel extending from said passage towards a respective inlet and outlet opening,
   - a pneumotachograph positioned in said passage and communicating with a pressure measuring device through openings provided in said mask to both sides of said pneumotachograph,
   - indicating and recording means attached to said pressure measuring device, and configured to indicate pressure before, during and immediately after each total occlusion, as well as air flow through said pneumotachograph,
   - an outlet valve mounted in said outlet channel,
   - an elastic balloon completely filled with a liquid and positioned in a portion of circular cross section of said inlet channel, said elastic balloon configured to be inflated until there is total occlusion of said inlet channel, to be completely deflated for free air flow through said inlet channel, as well as to be partly inflated to cause a predesignated air flow resistance in said inlet channel, and
   - a hand-operated syringe including a cylinder and a piston, remote from said face mask and communicating with said balloon through inelastic piping, both said syringe and piping being completely filled with liquid, said syringe being configured to inflate and to deflate said balloon in accordance with a position of said piston in said cylinder.

2. The apparatus of claim 1, wherein an inlet valve is positioned in said inlet channel downstream of said balloon.

3. The apparatus of claim 1, wherein said syringe includes a spring configured to urge said piston into a position defining deflation of said balloon.

4. The apparatus of claim 3, wherein said syringe contains an internal sleeve lengthwise movable in said cylinder by means of a screw-thread into a predesignated position defining the partial inflation of said balloon by holding said piston in a predesignated position.

5. The apparatus of claim 1, wherein said inlet channel is of cylindrical configuration with has an end closed and is provided with inlet openings in a wall of said cylindrical inlet channel.

6. The apparatus of claim 5, wherein a cylindrical membrane is positioned around said inlet openings remote therefrom, said membrane being connected by piping to an air-filled syringe configured to inflate said membrane so as to occlude said inlet openings and thereby occlude said inlet channel.

7. The apparatus of claim 6, wherein said membrane is inflatable by means of a hand-operated cylinder-piston unit connected to said membrane by piping, said unit having an open proximate end and a closed distal end, an air inlet in a side wall of said cylinder close to said proximate end and an outlet opening connected to said piping in the side wall of said cylinder distanced from said distal end, whereby said piston while being pushed inside said cylinder and pressing air through said piping into said membrane causes air from said membrane to be released into ambient atmosphere after having passed said outlet opening to said distal end.

8. The apparatus of claim 6, wherein said membrane is connected to computer means configured to inflate and deflate said membrane in accordance with a defined program.

9. The apparatus of claim 1, wherein said balloon is connected by piping to said syringe and to a second syringe filled with said liquid, said second syringe being separated from said piping by a valve to be opened to refill the apparatus with liquid by operating said second syringe.

10. The apparatus of claim 9, wherein said second syringe serves to titrate said apparatus.

11. An apparatus for measuring airways resistance of a person by occluding exhalation of said person during a short interval and for measuring collapsibility of the airways of the person by gradually increasing flow resistance through said apparatus, said apparatus comprising:
   - a face mask of a solid material adapted to be tightly attached to face portions of the person surrounding at least a nose of the person, said mask having a plenum close to the face portions, continued by a passage of smaller dimensions and an inlet channel and an outlet channel extending from said passage towards a respective inlet and outlet opening,
   - a pneumotachograph positioned in said passage and communicating with a pressure measuring device through openings provided in said mask to both sides of said pneumotachograph,
   - indicating and recording means attached to said pressure measuring device, and configured to indicate pressure before, during and immediately after each total occlusion, as well as air flow through said pneumotachograph,
   - an inlet valve mounted in said inlet channel,
   - an outlet valve mounted in said outlet channel,
   - an elastic balloon completely filled with a liquid and positioned in a portion of circular cross section of said outlet channel, said elastic balloon configured to be inflated until there is total occlusion of said outlet channel, to be completely deflated for free air flow through said outlet channel, as well as to be partly inflated to cause a predesignated air flow resistance in said outlet channel, and a hand operated syringe including a cylinder and a piston, remote from said face mask and communicating with said balloon through inelastic piping, both said syringe and piping being completely filled with liquid, said syringe being configured to inflate and to deflate said balloon in accordance with a position of said piston in said cylinder.

* * * * *